United States Patent [19]

Taylor

[11] Patent Number: 5,562,605

[45] Date of Patent: Oct. 8, 1996

[54] MEDIAL COLLATERAL LIGAMENT BRACE

[75] Inventor: Dean A. Taylor, Vancouver, Canada

[73] Assignee: Generation II Orthotics Inc., Richmond, Canada

[21] Appl. No.: 288,370

[22] Filed: Aug. 10, 1994

[51] Int. Cl.$^6$ ........................................................ A61F 5/00
[52] U.S. Cl. ................................................. 602/26; 602/16
[58] Field of Search .................................. 602/4, 16, 26, 602/23

[56] References Cited

U.S. PATENT DOCUMENTS

| 1,666,846 | 4/1928 | Cooper . | |
|---|---|---|---|
| 3,473,527 | 10/1969 | Spiro . | |
| 3,902,482 | 9/1975 | Taylor . | |
| 4,024,584 | 5/1977 | Smith . | |
| 4,287,885 | 9/1981 | Applegate . | |
| 4,296,744 | 10/1981 | Palumbo . | |
| 4,466,428 | 8/1984 | McCoy . | |
| 4,490,855 | 1/1985 | Figgie, III et al. . | |
| 4,765,318 | 8/1988 | Tranberg et al. . | |
| 4,793,333 | 12/1988 | Marquette . | |
| 4,796,610 | 1/1989 | Cromartie | 602/26 |
| 4,805,606 | 2/1989 | McDavid, III . | |
| 4,966,133 | 10/1990 | Kausek . | |
| 5,016,621 | 5/1991 | Bender . | |
| 5,133,341 | 7/1992 | Singer et al. | 602/16 |
| 5,230,697 | 7/1993 | Castillo et al. . | |
| 5,277,698 | 1/1994 | Taylor . | |
| 5,302,169 | 4/1994 | Taylor | 602/26 |
| 5,383,845 | 1/1995 | Nebolon | 602/26 |

FOREIGN PATENT DOCUMENTS

| 0050769 | 10/1981 | European Pat. Off. . | |
|---|---|---|---|
| 2136294 | 3/1983 | United Kingdom . | |
| 2136294 | 9/1994 | United Kingdom | 602/26 |

Primary Examiner—Richard J. Apley
Assistant Examiner—Kim M. Lee
Attorney, Agent, or Firm—Townsend and Townsend and Crew; Paul W. Vapnek; John T. Raffle

[57] ABSTRACT

A knee brace having a force strap to extend, when worn by a patient, from a first anchor position on the brace, above the patient's knee, behind the knee to a second anchor position on the brace, below the patient's knee. The brace has a stabilizer for the strap to maintain the force strap in position over the patient's femoral condyle.

3 Claims, 2 Drawing Sheets

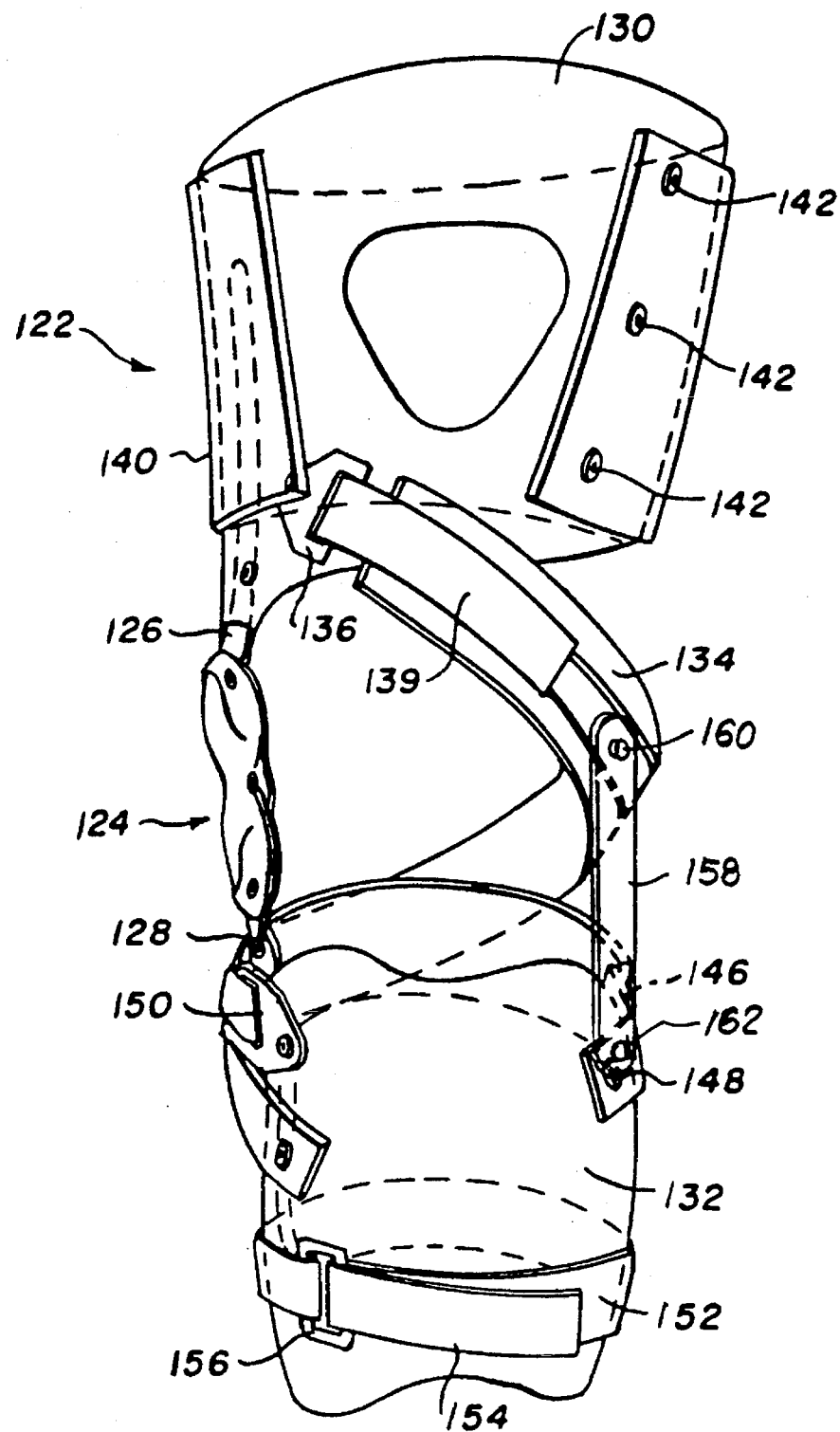

MEDIAL COLLATERAL LIGAMENT BRACE

FIELD OF THE INVENTION

This invention relates to a knee brace.

DESCRIPTION OF THE PRIOR ART

The knee is located between the femur (or thigh bone) and tibia (or shin bone). The knee is controlled by ligaments and cartilage. Contact between the femur and the tibia occurs across the cartilage and there are compartments or spaces at each side of the knee, the medial compartment on the inside of the knee and the lateral compartment on the outside.

The ligaments of knee can be damaged quite easily. Damage to the ligaments is common in a large number of athletic activities, perhaps particularly in football and skiing.

Applicants have developed a knee brace that is useful for medial collateral ligament injury. This ligament brace comprises a flexible sleeve, generally of neoprene, that fits over the knee and extends a substantial way up the femur and down the tibia. There is a hinge with rigid limbs extending from the hinge. The neoprene sleeve is reinforced with ribs that extend around the front of the tibia and back of the femur. These ribs act as anchoring points both for the limbs and for the straps that are used to tighten the brace to locate it on the patient. What is called a force strap is used to apply pressure over the medial femoral condyle.

A problem with this brace has been the movement of the force strap. In certain circumstances it can move up over the femoral condyle and, as a result, relaxes. When it does relax, it is, of course, not as effective as when it is properly tensioned.

The present invention solves this problem with medial collateral ligament braces and has proved to be strikingly effective in this regard.

Another ailment of the knee is uni-compartmental osteoarthritis which may occur in the medial or in the lateral compartment. With this ailment there is a mechanical malfunction of the knee. An uneven distribution of pressure occurs across the knee, causing excessive wear on the inside of the knee joint in medial compartmental osteoarthritis and on the outside in lateral compartmental osteoarthritis.

Our U.S. Pat. No. 5,277,698, issued Aug. 18, 1993 relates to a knee bracing method that reduces the effect of uni-compartmental osteoarthritis. Force is applied to the knee on that side of the knee remote from the compartment having osteoarthritis as the knee moves to extension. The force is applied at a point about 10° to 15° posterior of the normal axis of rotation of the knee.

This method has proved to be an extremely effective method of ameliorating the effects of uni-compartmental osteoarthritis but a problem can occasionally occur if the force strap, which is the strap that applies the force to the knee at a point about 10° to 15° posterior of the normal axis of rotation, moves from its effective position. The knee brace useful in the above method typically includes relatively rigid cuffs, one to be received around the femur and one to be received around the tibia. A hinge, having rigid limbs extending from it, is attached by those limbs to the cuffs. This brace generally is described and claimed in, for example, commonly owned U.S. Pat. No. 5,302,169, issued Apr. 12, 1994 and U.S. Pat. No. 3,902,482 issued Sep. 2, 1975. These disclosures are specifically incorporated herein by reference.

In general with braces of this type the force strap location has been changed, if necessary, by altering the fastening points. However, in a few, difficult osteoarthritis cases the strap can still move from its ideal position as defined above. The present invention is useful in those cases where the strap moves.

SUMMARY OF THE INVENTION

Accordingly, and in a first aspect, the present invention is a knee brace having a force strap to extend, when worn by a patient, from a first anchor position on the brace, above the patient's knee, behind the knee, to a second anchor position on the brace, below the patient's knee, and is the improvement comprising a stabilizer for the strap to maintain the force strap in position over the patient's femoral condyle.

In one aspect, the invention is a brace for the treatment of medial collateral ligament injury and comprises a sleeve to be worn around the knee, upper and lower ribs, linked by a hinge member, and a force strap extending from a first anchor point on the upper rib to a second anchor point on the lower rib, a housing on the sleeve to receive the force strap and maintain the strap over the medial femoral condyle.

In a further aspect, the invention is a brace for the treatment of uni-compartmental osteoarthritis and has a tibial cuff and a femoral cuff, linked by a hinge member, and straps to maintain the brace in position and in which the first anchor point is on the femoral cuff and the second anchor point on the tibial cuff, the stabilizer comprising a member extending from one cuff to the force strap.

Desirably the member extends from the tibial cuff to the strap in this further aspect of the invention.

DESCRIPTION OF THE DRAWINGS

The invention is illustrated, by way of example, in the drawings in which:

FIG. 2 is a front view of a second aspect of the invention.

DESCRIPTION OF THE PREFERRED EMBODIMENTS

Figure 1:
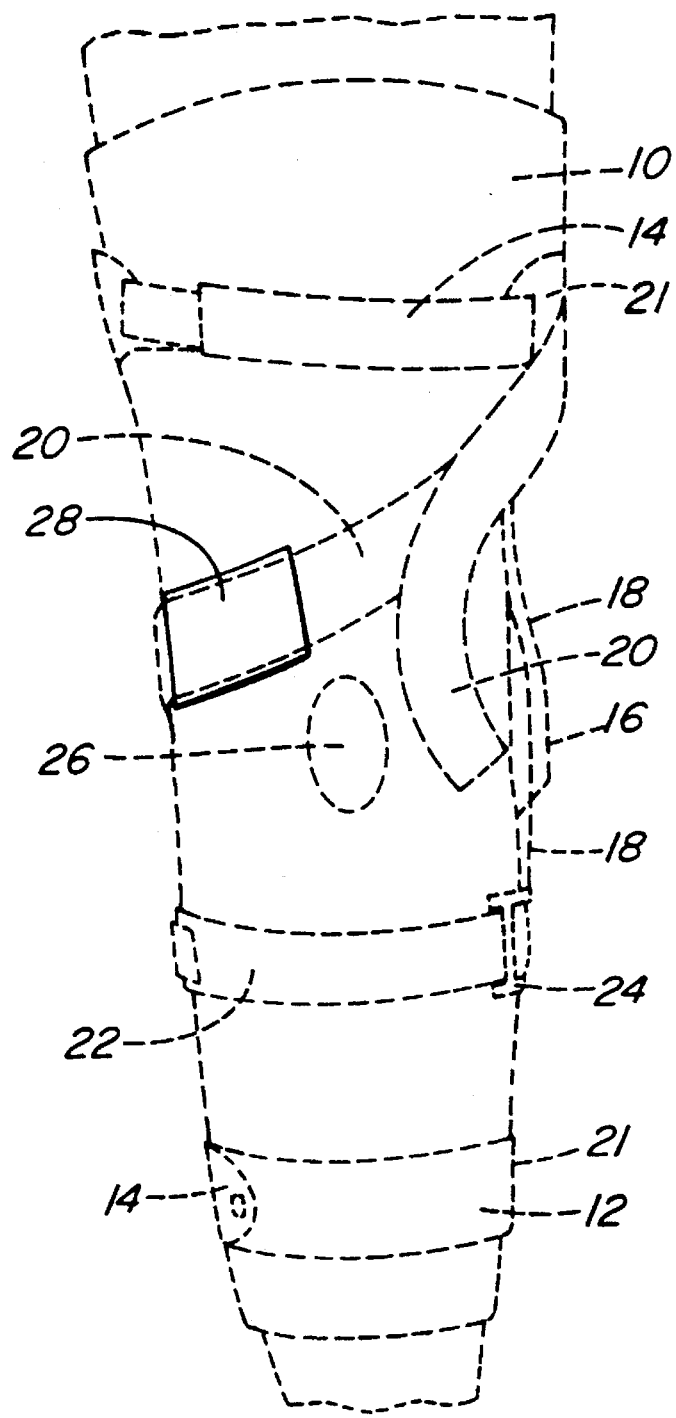
FIG. 1 is a front view of a brace according to one aspect of the present invention.

FIG. 1 shows a brace useful for the treatment of medial collateral ligament injury. It comprises a sleeve 10 with built-in relatively rigid ribs 12 of approximately semi-circular shape at the top and bottom. The upper rib extends behind the leg, the lower in front of the leg. The ends of the semi-circular ribs are attached by straps 14. There is a hinge 16 and members 18 extend from it. Such hinges are well known in the art, for example, from the U.S. Pat. Nos. 5,302,169 and 3,902,482 referred to above. There is a strap 20 which may be described as a force strap, which extends around the wearer's leg, from anchor points 21 on the ribs 12. The straps 14, 20 and 22 are engaged in eyelets 24 and are provided with hook and eye fasteners, for example those available under the trademark VELCRO.

The sleeve 10 includes an opening 26 that generally fits over the knee cap of the wearer and assists in location of the sleeve 10 on the patient.

Force strap 20 extends from its first anchor point, above the knee, behind the knee to a second anchor point on the lower rib 12, below the patient's knee.

There is a stabilizer for the strap to maintain the force strap 20 precisely in position over the patient's femoral condyle over which the strap normally passes when properly adjusted. In FIG. 1 that stabilizer comprises a housing 28 on the sleeve 10 that receives the strap 20, preventing it from moving upwardly or downwardly but keeping it firmly positioned over the medial femoral condyle. The housing 28 may be a simple material pocket, firmly attached to the sleeve 10. It is desirably provided with part of a hook and eye attachment on its outer surface to engage the hook or eye fastener of the force strap.

Using the strap of FIG. 1 extremely good results have been achieved in alleviating the effects of medial collateral ligament damage.

The embodiment of FIG. 2 shows a knee brace that would typically be used for the alleviation of uni-compartmental osteoarthritis. But such a brace can be used in all aspects of knee support.

The brace 122 of FIG. 2 has a hinge 124 having rigid limbs 126 and 128 extending from it. Limb 126 is attached to an upper cuff 130 and limb 128 is attached to a lower cuff 132. The upper cuff 130 is located above the knee and the lower cuff 132 below the knee. The hinge 124 joining the cuffs is adjacent the knee and, more particularly, adjacent the compartment that has osteoarthritis.

Cross force strap 134 is pivotally anchored to the upper cuff at bracket 136 and extends around the knee to a pivotal connection to the lower cuff 132. The bracket 136 has an opening through which the force strap 134 can extend. Again the strap 134 is provided with hook and eye fasteners 139. This is desirable in these knee braces because these fasteners permit a wide range of adjustments. Strap 134 is led through the bracket 136, back on itself, to be fastened to itself by the hook and pile fastener. There may be a soft foam plastic cuff attached to the force-strap 134 to make contact with the wearer.

The upper cuff 130 includes a thigh strap 140 extending from anchor points 142 and, again, having a hook or pile fastener at one end to mate with a hook or pile anchor point on the upper cuff 130. In this way, the upper cuff 130 is securely attached to the thigh of a wearer. Beneath the knee the lower cuff 132 is attached by an upper strap 146 extending from a pivotal anchor point 148, around through attachment bracket 150 and back on itself, again using hook and pile fasteners.

There is a second lower strap 152 on the lower cuff 132 to attach the cuff around the calf of the wearer. Again the preferred form of attachment is by hook and pile pieces 154 positioned on strap 152 with the strap able to extend through a bracket 156 back on itself.

According to the present invention, there is a stabilizer, typically in the form of a relatively rigid bar, extending from a pivotal anchor point on the cuff 132 upwardly to an anchor point on the force strap 134.

The brace of FIG. 2 is attached to a patient precisely as described, for example, in the above U.S. Pat. No. 5,277,698. However, the feature of the present invention is that after fitting, a stabilizer 158 is located at the pivotal anchor points 160 and 162 and acts to maintain the force strap 134 precisely in the desired position, that is over the femoral condyle.

The location of the brace in the correct position is carried out in well known manner. Using the present invention, the location of the strap 134, which in certain difficult cases has been a problem with prior art braces, is no longer a problem as the stabilizer 158 ensures that the position of the strap 134 is, in effect, determined by the unvarying position of the lower cuff 132. The strap 134 cannot rise over the femoral condyle and relax, as has happened in the prior art.

The present invention thus provides a simple, economical but effective method of ensuring that the force strap, which is an important aspect of the two braces, remains in the correct position.

Although the forgoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

I claim:

1. In a knee brace having a sleeve adapted to be worn about the knee and a force strap to extend, when worn by a patient, from a first anchor position behind the knee, to a second anchor position on the brace, below the patient's knee, the improvement comprising a stabilizer coupled to the force strap, said stabilizer comprising a pocket coupled to said sleeve for receiving at least a portion of the force strap and preventing upward and downward movement of said force strap to maintain said force strap in a fixed position over the medial femoral condyle.

2. In a knee brace having a femoral cuff and a tibial cuff, linked by a hinge member, and a force strap to extend, when worn by a patient, from a first anchor position on the brace, above the patient's knee, behind the knee, to a second position on the brace, below the patient's knee, the improvement comprising a stabilizer coupled to said force strap, the stabilizer comprising an elongate rigid bar member extending from a pivotal anchor point positioned on said tibial cuff upwardly to an anchor point on said force strap to maintain said force strap in a fixed position over the patient's femoral condyle, said fixed position being determined by the unvarying position of said tibial cuff.

3. The knee brace of claim 1 wherein the force strap includes a first fastener, the pocket comprising a second fastener for cooperating with the first fastener to fix the force strap to the pocket.

\* \* \* \* \*

UNITED STATES PATENT AND TRADEMARK OFFICE
CERTIFICATE OF CORRECTION

PATENT NO.         : 5,562,605
APPLICATION NO.    : 08/288370
DATED              : October 8, 1996
INVENTOR(S)        : Taylor Page 1 of 1

It is certified that error appears in the above-identified patent and that said Letters Patent is hereby corrected as shown below:

Col. 4 lines 28-37 should read

1. In a knee brace having a sleeve adapted to be worn about the knee and a force strap to extend, when worn by a patient, from a first anchor position on the brace, above the patient's knee, behind the knee, to a second anchor position on the brace, below the patient's knee, the improvement comprising a stabilizer coupled to the force strap, said stabilizer comprising a pocket coupled to said sleeve for receiving at least a portion of the force strap and preventing upward and downward movement of said force strap to maintain said force strap in a fixed position over the patients medial femoral condyle.

Signed and Sealed this
Twentieth Day of September, 2011

David J. Kappos
*Director of the United States Patent and Trademark Office*